United States Patent
Sagae et al.

(10) Patent No.: US 6,753,437 B1
(45) Date of Patent: Jun. 22, 2004

(54) CVD MATERIAL COMPOUND AND METHOD FOR MANUFACTURING THE SAME, AND CVD METHOD OF IRIDIUM OR IRIDIUM COMPOUND THIN FILM

(75) Inventors: Takeyuki Sagae, Shinmachi (JP); Jun-ichi Taniuchi, Shinmachi (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 0 days.

(21) Appl. No.: 10/348,345

(22) Filed: Jan. 22, 2003

(51) Int. Cl.$^7$ .................. C07F 15/00; C23C 16/00
(52) U.S. Cl. .................. 556/40; 556/136; 106/1.28; 106/297.18; 427/587; 427/593
(58) Field of Search ............. 556/40, 136; 106/1.28; 106/287.18; 427/587, 593

(56) References Cited

U.S. PATENT DOCUMENTS 6,555,701 B2 * 4/2003 Saito et al. .................. 556/40
6,663,706 B2 * 12/2003 Saito et al. ............ 106/287.18

FOREIGN PATENT DOCUMENTS

| JP | 08-085873 | 4/1996 |
| JP | 09-049081 | 2/1997 |
| JP | 11-292888 | 10/1999 |

OTHER PUBLICATIONS

J. Vac. Sci. Technol. A 18(1), Jan./Feb. 2000, "Precursor chemistry and film growth with (methylcyclopentadienyl) (1,5–cyclooctadiene) iridium", pp. 10–16, 2000.

* cited by examiner

*Primary Examiner*—Porfirio Nazario-Gonzalez
(74) *Attorney, Agent, or Firm*—Rothwell, Figg, Ernst & Manbeck, P.C.

(57) ABSTRACT

The present invention relates to a raw material for CVD comprising an organic iridium compound as a main component, said organic iridium compound being tris(2,4-octanedionato)iridium represented by Formula 1. Particularly preferably, the raw material for CVD consists only of the trans isomer of tris(2,4-octanedionato)iridium.

11 Claims, 1 Drawing Sheet

CVD MATERIAL COMPOUND AND METHOD FOR MANUFACTURING THE SAME, AND CVD METHOD OF IRIDIUM OR IRIDIUM COMPOUND THIN FILM

BACKGROUND OF THE INVENTION

1. Field of the Invention

The present invention relates to a raw material used for the production of an iridium- or iridium compound-thin film by CVD method, and a production method thereof.

2. Description of the Related Art

In recent years, iridium or noble metals such as iridium have been used as thin film electrode materials for various types of semiconductor devices such as DRAM or FERAM. This is because these noble metals have a low specific resistance, and therefore they have excellent electric properties when they are used as electrodes. Especially, iridium and an oxide thereof are used as electrodes for FERAM.

Chemical vapor deposition method (hereinafter referred to as CVD method) is commonly used to produce a thin film used for thin film electrodes, as well as sputtering method. CVD method enables the production of a homogeneous thin film, and this method is superior to sputtering method especially in step coverage (an ability to cover steps). Particularly, in order that memory devices such as the above DRAM or FERAM have a large capacity, it is attempted to change the structure from a two-dimensional multi-layer film to a three-dimensional multi-layer film. The formation of such a complicated electrode structure requires step coverage and a film formation control ability, which are stricter than the previous ones. The CVD method is likely to become a major production process of thin film electrodes, since it can meet a recent requirement for higher densification of circuits and electronic components.

Properties generally required for a raw-material used for CVD method are that it has a low melting point and so it is in a liquid state at ordinary temperature, and that it has a high vapor pressure. Compounds previously known to be used as raw materials for iridium films and iridium compound thin films which are produced by CVD method are broadly divided into β-diketone iridium compounds and cyclooctadiene iridium compounds.

The β-diketone iridium compound is a complex of iridium and a β-diketone organic compound. As β-diketone organic compounds used as raw materials for CVD, several organic iridium compounds represented by the undermentioned formula have ever been known. Although these iridium compounds are solid at ordinary temperature, they have a melting point (approximately 140° C. to 270° C.) which is significantly lower than that of the previously known iridium compounds. Moreover, these iridium compounds have a high sublimation property and a high vapor pressure at low and medium temperature, and there is a clear difference between the vaporization temperature and the decomposition temperature. Therefore, these iridium compounds are considered to be extremely advantageous in the production of a film by CVD according to sublimation method (for the details of β-diketone iridium compounds used as raw materials for CVD, please refer to Japanese Patent Laid-Open Nos. 9-49081 and 8-85873).

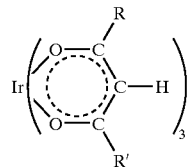

Formula 1 wherein each of R and R' is any one of $CH_3$, CF, $CF_3$, $C_2H_5$, $C_2F_5$, $C_3H_7$, $C_3F_7$ and $C(CH_3)_3$.

On the other hand, the cyclooctadiene iridium compound is a compound obtained by coordinating cyclooctadiene and a cyclodiene derivative with iridium. Examples of cyclooctadiene iridium compounds known to be used as raw materials for CVD include methylcyclopentadienyl(1,5-cyclooctanedione)iridium, ethylcyclopentadienyl(1,5-cyclooctanedione)iridium and others, which are represented by the following formula:

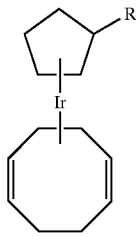

Formula 2 wherein R represents any one of hydrogen, a methyl group and an ethyl group.

These cyclooctadiene iridium compounds have a further lower melting point (approximately 25° C. to 40° C.). Of these, ethylcyclopentadienyl(1,5-scyclooctanedione)iridium is liquid at ordinary temperature and therefore it has the advantage of being vaporized without using the sublimation method (for the details of cyclooctadiene iridium compounds, please refer to Japanese Patent Laid-Open No. 11-292888 and J. Vac. Sci. Technol. A 18(1) 10–16 (2002)).

However, the present inventors point out that these organic iridium compounds have problems in terms of the industrial production efficiency and applicable range of iridium thin films, which are described below.

Concerning β-diketone iridium compounds, the previously known β-diketone iridium compound is in a solid state at ordinary temperature, although it has a low melting point. Accordingly, the sublimation method is applied to form a thin film using the β-diketone iridium compound as a raw material for CVD. However, vaporization by the sublimation method is an unstable process, and it is relatively difficult to keep constant the vaporized amount obtained by sublimation. Moreover, even though the vaporized amount can be controlled, it is difficult to maintain the vaporized compound in a gaseous state, and there may be cases that raw material gas is returned to a solid state and attached to the inner surface of a piping in the step of transporting the gas from a raw material container to a substrate. As a result, there may be a risk that the film production rate becomes unstable and the morphology of a thin film deteriorates.

In contrast, a cyclooctadiene iridium compound, another known organic iridium compound, is liquid at ordinary temperature, and so a thin film can be produced by the vaporization of the compound by heating without applying the sublimation method. However, according to the present inventors' studies, this cyclooctadiene iridium compound has poor reactivity with oxygen, and so, even though film production is carried out in an oxygen atmosphere, an iridium oxide thin film cannot be produced, but a pure iridium thin film is produced instead. Taking into consideration the fact that it is iridium oxide that is considered to be applied as a thin film electrode for FERAM, it cannot but say that the applicable range of the cyclooctadiene iridium compound is narrow.

The present invention was made against the above described background. It is the object of the present invention to provide an iridium compound used as a raw material for CVD for producing an iridium- or iridium compound-thin film, wherein the iridium compound has a low melting point, it is in a liquid state at ordinary temperature, and it can stably be vaporized and has good reactivity with oxygen, so that an iridium oxide thin film as well as an iridium thin film can be produced from the compound; and a production method thereof.

SUMMARY OF THE INVENTION

As a result of intensive studies by the present inventors directed toward the above object, they have found the object can be achieved with the use of tris(2,4-octanedionato) iridium that is one type of β-diketone iridium, thereby completing the present invention.

That is to say, the present invention relates to a raw material for CVD comprising an organic iridium compound as a main ingredient, wherein the organic iridium compound consists of tris(2,4-octanedionato)iridium represented by the following formula:

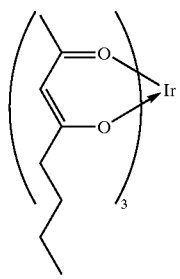

Formula 3

This tris(2,4-octanedionato)iridium is one form of β-diketone iridium, and it is liquid at ordinary temperature. Accordingly, this compound easily vaporizes when it is used in the production of a film, and raw materials can quantitatively be supplied by means such as gas bubbling or a liquid mass flow controller. Moreover, this organic iridium compound has good stability, having a low possibility that it has phase change or decomposition during the process of being transported to a substrate. Thus, the use of the iridium compound of the present invention enables the formation of a thin film at a stable film production rate and the efficient production of a morphologically good thin film.

Furthermore, this tris(2,4-octanedionato)iridium has relatively good reactivity when it is heated on a substrate, and iridium oxide can be deposited by reaction in an oxygen atmosphere. Accordingly, the iridium compound of the present invention is preferably used as a raw material for producing an iridium oxide thin film, and this compound has an applicable range broader than the conventional cyclooctadiene iridium compounds.

According to the present inventors' studies, tris(2,4-octanedionato)iridium includes geometric isomer such as cis isomer and trans isomer. Consequently, it is considered that depending on production methods, tris(2,4-octanedionato) iridium is obtained in a mixed state of cis isomer and trans isomer. Hence, the present inventors have studied the properties of a thin film produced when such tris(2,4-octanedionato)iridium comprising these two types of geometric isomer is used as a raw material for CVD, and as a result, they have found that the use of a raw material comprising both cis isomer and trans isomer is not preferable, if the morphology of a thin film is considered.

This is because geometric isomer is represented by the same molecular formula, but these physical properties are vastly different from one another. In terms of the physical properties of geometric isomer as raw materials for CVD, the vaporization rate and decomposition rate of the geometric isomer are considered to be different. Therefore, where a film is produced from a compound in which geometric isomer are mixed according to CVD method, a constant film production rate is hardly obtained, and as a result, the morphology of the thin film deteriorates.

Based on the above considerations, the present inventors have thought that a preferred raw material for CVD which is more stably vaporized would only consist of either the cis isomer or the trans isomer of tris(2,4-octanedionato)iridium, and they have made a study of it. As a result of the study, the present inventors have found that trans isomer is liquid at ordinary temperature whereas cis isomer are solid at ordinary temperature. Thus, the present inventors have thought that the most preferred iridium compound as a raw material for CVD would only consist of the trans isomer of tris(2,4-octandionato)iridium. This compound used as a raw material for CV consisting of trans-tris(2,4-octanedionato)iridium is in a liquid state at room temperature, and it easily enables the supply and vaporization of raw materials. In addition, this compound has a stable vaporization rate, therefore enabling efficient production of a morphologically excellent iridium- or iridium compound-thin film.

Next, the production method of the tris(2,4-octanedionato)iridium of the present invention will be explained. Basically, this production method of tris(2,4-octanedionato)iridium comprises the steps of reacting substances that are raw materials for this organic iridium compound so as to synthesize tris(2,4-octanedionato) iridium, extracting tris(2,4-octanedionato)iridium of interest from a reaction solution after the reaction, and removing unreacted 2,4-octanedione from an extractant.

First, for the synthesis of tris(2,4-octanedionato)iridium, an iridium compound such as iridium chloride and 2,4-octadione are reacted in a solvent. In terms of reactivity, a preferred iridium compound is iridium chloride and a preferred solvent is water. This reaction system requires the addition of alkali bicarbonate such as potassium bicarbonate. The addition of alkali bicarbonate is carried out to control the pH of the reaction system and to promote the reaction of the iridium compound and 2,4-octadione, which is a neutralization reaction. A range of pH for the reaction system is preferably set in an alkaline region, and particularly preferably within a range of pH 7 to 9. In an acid region of less than pH 7, the synthesis reaction does not progress, and therefore the yield of tris(2,4-octanedionato)iridium decreases. Further, the reason why pH 9 is set at the maximum value in the alkaline region is that the reaction rate decreases again if the actual pH exceeds pH 9, and in this case also, the yield of tris(2,4-octanedionato)iridium decreases. The reaction temperature and the reaction time are preferably set at 90° C. to 100° C. and 7 to 9 hours, respectively.

The reaction solution obtained after the reaction contains unreacted iridium compounds, which should be eliminated by extracting the solution. The extraction process comprises the steps of contacting an extractant with the reaction solution and extracting tris(2,4-octanedionato)iridium into the extractant. A nonpolar solvent, particularly benzene, is preferably used for the extractant. Preferably, this extraction process is carried out repeatedly so as to completely recover tris(2,4-octanedionato)iridium from the reaction solution.

On the other hand, the extractant obtained after the extraction process contains unreacted 2,4-octanedione, which should be removed. In order to efficiently purify and recover tris(2,4-octanedionato)iridium, it is appropriate that this step of removing 2,4-octanedione should be carried out by distillation (vacuum distillation). Considering the boiling point of 2,4-octanedione, this distillation is preferably carried out by vacuum distillation at a pressure of 10 to 150 Pa and at a temperature of 35° C. to 45° C.

Unreacted 2,4-octanedione is removed by the above vacuum distillation, and tris(2,4-octanedionato)iridium collected as a fraction is considered to have such purity that the compound can be used as a raw material for CVD. However, the present inventors have studied and confirmed that in a case where vacuum distillation is carried out only in consideration of the separation of 2,4-octanedione, 2,4-octanedione can be removed, but the purity of tris(2,4-octanedionato)iridium isolated is not necessarily high. The present inventors have considered that this is because, in the reaction process, not only an unreacted raw material (an iridium compound, 2,4-octanedione) and a reaction product of interest (tris(2,4-octanedinato)iridium) but also unexpected side reaction product is generated in the reaction system, and that this byproduct is associated with the fraction in the above vacuum distillation.

Thus, the present inventors have studied a method for removing such a byproduct to solve the above described problem. As a result, the present inventors have not clarified the specific name (chemical composition) of the substance, but they have found that the boiling point of the substance is higher than those of 2,4-octanedione and tris(2,4-octanedionato)iridium. The present inventors have considered that, in order to remove the byproduct, it is appropriate that the fraction obtained by the above vacuum distillation is again subjected to distillation. According to the present inventors, the appropriate conditions for the vacuum distillation are a pressure of 0.1 to 1.5 Pa and a temperature of 140° C. to 200° C. The conditions should be determined within the above ranges for the reasons that the distillation temperature should be low, because if the distillation temperature is set high, tris(2,4-octanedionato)iridium may decompose, and that the degree of vacuum should be low to collect tris(2,4-octanedionato)iridium.

By this redistillation, 99% or more tris(2,4-octanedionato)iridium can be produced. As stated above, tris(2,4-octanedionato)iridium includes geometric isomer such as trans isomer and cis isomer. Therefore, tris(2,4-octanedionato)iridium produced by the above method is also likely to be a mixture of such geometric isomer.

Hence, it can be said that tris(2,4-octanedionato)iridium produced by the above described method is preferably subjected to an operation of separating geometric isomer. In this method of separating geometric isomer, the produced tris(2,4-octanedionato)iridium is preferably passed through column chromatography. This separation operation is particularly preferably carried out by liquid chromatography using octadecylsilane as a solid phase and alcohol (ethanol, isopropyl alcohol, etc.) as a mobile phase.

Lastly, a thin film production method which uses a raw material for CVD-comprising the tris(2,4-octanedionato) iridium of the present invention as a main ingredient will be explained. This thin film production method is basically the same as a common CVD method. That is to say, the thin film production method comprises vaporizing a raw material for CVD, transferring it onto a substrate, and decomposing it thereon, so that iridium or an iridium compound is deposited. The temperature of heating the raw material for CVD of the present invention is preferably set at 150° C. to 200° C.

A method for decomposing the raw material molecule vaporized and transferred onto the substrate surface is not particularly limited, and any method such as heating CVD method or plasma CVD method can be adopted. Of these, heat CVD method is particularly preferable because this method uses simple devices and also because the raw material substance of the present invention has a relatively low decomposition temperature and so there is no risk of damaging the substrate. Moreover, it is preferable to set the temperature of the substrate at 350° C. to 400° C. to decompose the iridium compound thereon.

Furthermore, in this CVD process, the inside of the reactor is preferably maintained in a reduced pressure atmosphere. This is because a uniform film thickness distribution and good step coverage (an ability to cover steps) can be obtained when the inside of the reactor is maintained in a reduced pressure atmosphere. The pressure of the inside of the reactor is preferably within a range of 500 to 700 Pa.

DETAILED DESCRIPTION OF THE PREFERRED EMBODIMENTS

Figure 1:
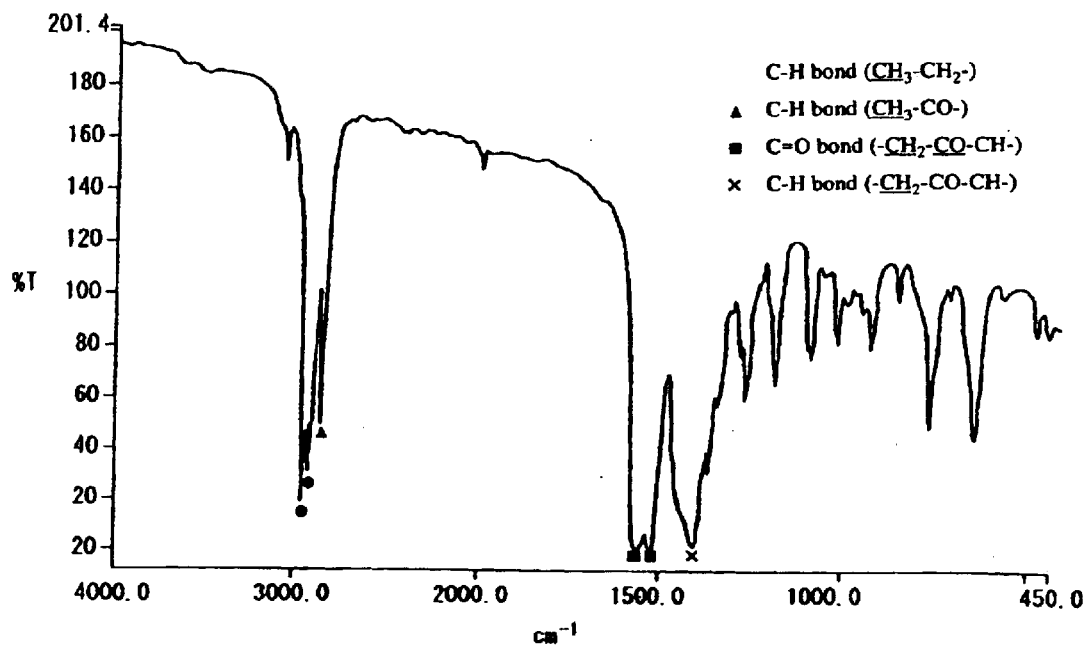
FIG. 1 is a view showing the IR spectrum of tris(2,4-octandionato)iridium produced in the first embodiment.

The present invention is further described in the following preferred embodiments while referring to the figures.

Embodiment 1; Production of the Organic Iridium Compound 32.5 g of iridium chloride trihydrate (87.5 mmol) and 38.64 g of 2,4-octadione (271.25 mmol) were brought to reflux by heating at 93° C. to 95° C. for 2 hours in a separable flask, using water as a solvent. Then, potassium bicarbonate was added so that the pH of the solution became 8.0 (the additive amount: 60.15 g). Thereafter, this solution was brought to reflux by heating at 93° C. to 95° C. for 5 hours so as to promote the reaction.

Thereafter, the obtained reaction solution is transferred to a separatory funnel and then extracted with benzene. This extraction was carried out 4 or 5 times repeatedly, so that the benzene layer became transparent. The weight of the thus obtained extract was reduced using a rotary evaporator, and after it was again extracted with water, anhydrous magnesium sulfate was added to the extract (a benzene layer) so as to dehydrate the extract. After the dehydration process, the extract was subjected to vacuum filtration to remove magnesium sulfate, and the remaining extract was condensed using a rotary evaporator. The thus obtained extract was a dark red liquid.

When the condensed extract was subjected to gas chromatography to examine the ingredients, peaks were observed at 3 retention times. Table 1 shows the positions of these three peaks and the mixing ratios of ingredients having these peaks.

[Table 1]

TABLE 1

| Retention Time | 4.28 min | 43.05 min | 44.84 min |
|---|---|---|---|
| Composition | 27.8% | 53.0% | 18.9% |

Of these peaks, the peak at retention time 4.28 min shows 2,4-octadione, both the peaks at 43.05 min and at 44.84 min show tris(2,4-octanedionato)iridium of interest. Accordingly, it is found that the concentration of tris(2,4-octandionato)iridium in the extract in this embodiment is 71.9%.

Next, in order to remove 2,4-octadione from this extract, vacuum distillation was carried out at 40 Pa (0.3 torr) at 40° C.

The fraction obtained by this vacuum distillation was a dark red syrup-like liquid having a high viscosity. When this dark red liquid was analyzed by gas chromatography, three peaks were observed. Table 2 shows the positions of these three peaks and the mixing ratios of ingredients having these peaks.

[Table 2]

TABLE 2

| Retention Time | 4.29 min | 42.49 min | 44.27 min |
|---|---|---|---|
| Composition | 2.65% | 72.49% | 24.91 % |

From the result shown in the table, it was confirmed that 2,4-octadione was removed by vacuum distillation and as a result, the purity of tris(2,4-octanedionato)iridium became 97.4%.

Thereafter, vacuum distillation was carried out again to remove a byproduct from tris(2,4-octanedionato)iridium produced at this stage and to purify the fraction. The conditions for this vacuum distillation were 66.5 Pa (0.5 torr) and 180° C.

The fraction obtained by this vacuum distillation was a red yellow liquid. The separated substance which seemed to be a byproduct was a black tarry liquid. When this red yellow liquid was analyzed by gas chromatography, as with in the extraction process, three peaks were observed. Table 3 shows the positions of these three peaks and the mixing ratios of ingredients having these peaks.

[Table 3]

TABLE 3

| Retention Time | 4.29 min | 42.49 min | 44.27 min |
|---|---|---|---|
| Composition | 0.26% | 73.49% | 26.25% |

From Table 3, it is found that 99% or more tris(2,4-octanedionato)iridium was purified and collected by this vacuum distillation.

Figure 2:
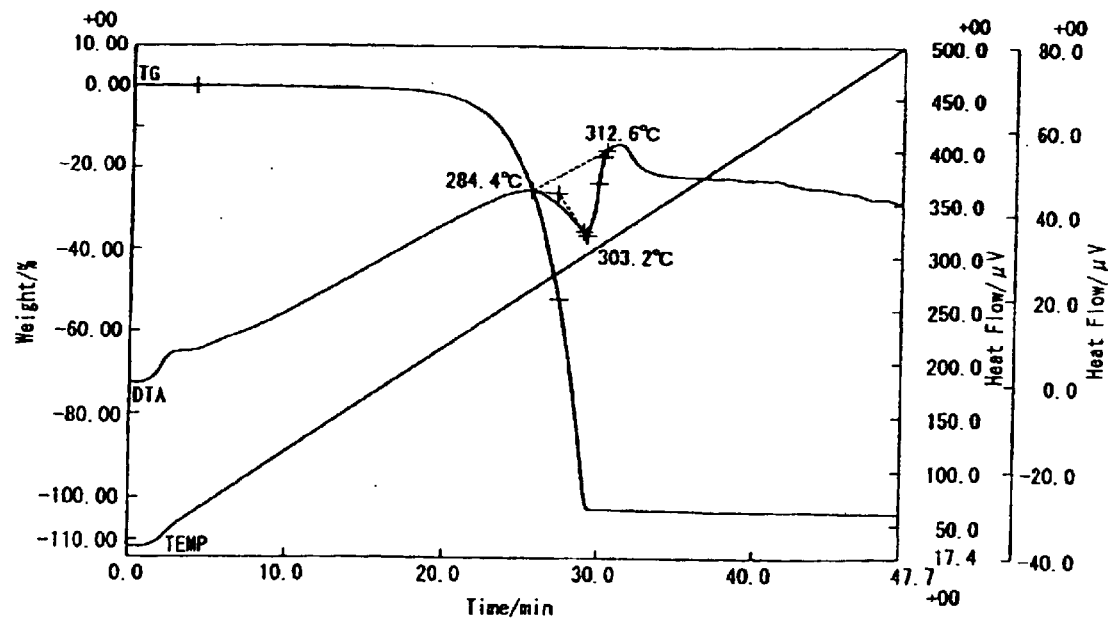
FIG. 2 is a view showing the TG-DTA curve of tris(2,4-octandionato)iridium produced in the first embodiment.

Thereafter, infrared absorption spectrum analysis (IR) was carried out on this tris(2,4-octanedionato)iridium to obtain a profile shown in FIG. 1. Moreover, thermnogravimetry/differential thermal analysis (TG/DTA) was carried out on this tris(2,4-octanedionato)iridium in an argon atmosphere at a temperature increase rate of 10° C./min to obtain the results shown in FIG. 2. From FIG. 2, it was confirmed that the total amount of tris(2,4-octanedionato)iridium produced in the present invention was vaporized at 500° C. and no nonvolatile ingredients which might become impurities were contained therein.

Further, as is clear from Table 3, there are two peaks at 42.49 min and at 44.27 min, which show peaks of tris(2,4-octanedionato)iridium. It is considered that these two peaked appeared because tris(2,4-octanedionato)iridium produced in this embodiment comprises mixed geometric isomer. The present inventors have studied and confirmed that the peak at 42.49 min is a trans peak and that at 44.27 min is a cis peak.

Next, the produced tris(2,4-octanedionato)iridium was passed through liquid column chromatography (the mobile phase is ethanol and the solid phase is octadecylsilane) to separate trans isomer so as to obtain trans-tris(2,4-octanedionato)iridium.

Comparative Test:

As with in the first embodiment, iridium chloride trihydrate and 2,4-octadione were brought to reflux using water as a solvent, and potassium bicarbonate was then added thereto for reaction. This time, reaction was carried out so that the pH of the reaction solution became 6.0. The reaction time and the reaction temperature were the same as in the first embodiment. Thereafter, the reaction solution obtained by the reaction was extracted with benzene in the same manner as in the first embodiment.

When the condensed extract was analyzed by gas chromatography, as with in the first embodiment, three peaks were observed, but the composition of the extract was different. Table 4 shows the positions of these three peaks and the mixing ratios of ingredients having these peaks.

[Table 4]

TABLE 4

| Retention Time | 4.28 min | 43.05 min | 44.84 min |
|---|---|---|---|
| Composition | 68.8% | 23.9% | 7.9% |

As is clear from Table 4, it was confirmed that when the pH of the solution was in the acid region during reaction, the residual rate of unreacted 2,4-octanedione became high and that the purity of tris(2,4-octanedionato)iridium was 31.8%, which was lower than the purity obtained when the solution was reacted in the alkali region.

Embodiment 2; Production of Iridium Oxide Thin Film

In the next step, using trans-tris(2,4-octanedionato) iridium produced in the first embodiment as a raw material, an iridium oxide thin film was produced by CVD method. In the CVD process, reaction conditions were set as follows:

Raw material heating temperature: 150° C.

Flow rate of carrier gas (argon): 45 sccm

Flow rate of reaction gas (oxygen): 45 sccm

Pressure of reactor: 530 Pa (4 torr)

Temperature of substrate: 350° C.

The morphology of the obtained iridium oxide thin film was examined with an AFM (atomic force microscope). As a result, it was confirmed that the value of surface roughness $R_{MS}$ is represented by $P_{MS}$=2.1 nm, so that a thin film having a good morphology can be produced.

What is claimed is:

1. CVD material compound comprising an organic iridium compound as a main component, wherein said organic iridium compound is tris(2,4-octanedionato)iridium represented by the following formula:

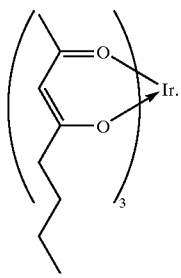

Formula 1

2. The CVD material compound according to claim 1, consisting only of the trans isomer of tris(2,4-octanedionato) iridium.

3. A method for manufacturing tris(2,4-octanedionato) iridium comprising the steps of:
preparing a mixture solution of an iridium compound and 2,4-octadione by mixing them in a solvent,
adding potassium bicarbonate to said mixture solution, so that the solution is maintained in an alkaline pH to promote formation of tris(2,4-octanedionato)iridium,
contacting the mixture solution obtained after the reaction with an extractant to form an extract comprising tris (2,4-octanedionate)iridium, and
removing unreacted 2,4-octanedione remaining in the extract.

4. The method for manufacturing tris(2,4-octanedionato) iridium according to claim 3, wherein the iridium compound is iridium chloride and the solvent is water.

5. The method for manufacturing tris(2,4-octanedionato) iridium according to claim 3, wherein the mixture solution is maintained within a range of 7–9 of pH during the reaction.

6. The method for manufacturing tris(2,4-octanedionato) iridium according to claim 3, wherein the extractant is benzene.

7. The method for manufacturing tris(2,4-octanedionato) iridium according to claim 3, wherein the extract is subjected to vacuum distillation at a pressure of 10 to 150 Pa and at a temperature of 35° C. to 45° C. to remove 2,4-octanedione therein.

8. The method for manufacturing tris(2,4-octanedionato) iridium according to claim 3, wherein a fraction distilled after the removal of 2,4-octanedione is again subjected to vacuum distillation at a pressure of 0.1 to 1.5 Pa and at a temperature of 140° C. to 200° C.

9. The method for manufacturing tris(2,4-octanedionato) iridium according to claim 8, comprising a further step wherein the distilled fraction is passed through a chromatographic column to separate the cis isomer from trans isomer of tris(2,4-octanedionato)iridium.

10. The method for manufacturing tris(2,4-octanedionato) iridium according to claim 9, wherein the step for separation of the cis isomer from the trans isomer is carried out by means of liquid chromatography using octadecylsilane as fixed phase and alcohol (ethanol, isopropyl alcohol, etc.) as mobile phase.

11. A chemical vapor deposition method for formation of a thin film from iridium or an iridium compound, which comprises vaporizing the raw material for CVD according to claim 1, transferring it onto a substrate, and decomposing it, so that iridium or the iridium compound is deposited on the substrate.

* * * * *